US011564645B2

(12) United States Patent
Milioni De Carvalho et al.

(10) Patent No.: US 11,564,645 B2
(45) Date of Patent: Jan. 31, 2023

(54) METHODS AND SYSTEMS FOR DIGITAL MAMMOGRAPHY IMAGING

(71) Applicant: GE Precision Healthcare LLC, Milwaukee, WI (US)

(72) Inventors: Pablo Milioni De Carvalho, Chaville (FR); Jorge Corsino Espino, Paris (FR); Vincent Jonas Bismuth, Paris (FR); Barbara Grosjean Leh, Orsay (FR)

(73) Assignee: GE Precision Healthcare LLC, Milwaukee, WI (US)

( * ) Notice: Subject to any disclaimer, the term of this patent is extended or adjusted under 35 U.S.C. 154(b) by 465 days.

(21) Appl. No.: 16/800,978

(22) Filed: Feb. 25, 2020

(65) Prior Publication Data

US 2021/0259649 A1   Aug. 26, 2021

(51) Int. Cl.
*A61B 6/00* (2006.01)
*A61B 6/12* (2006.01)
*G06T 7/70* (2017.01)
*G06T 5/00* (2006.01)
*G06T 7/00* (2017.01)

(52) U.S. Cl.
CPC ............... *A61B 6/12* (2013.01); *A61B 6/463* (2013.01); *A61B 6/469* (2013.01); *A61B 6/481* (2013.01); *A61B 6/482* (2013.01); *A61B 6/502* (2013.01); *A61B 6/5235* (2013.01); *G06T 5/009* (2013.01); *G06T 7/0014* (2013.01); *G06T 7/70* (2017.01); *G06T 2207/30068* (2013.01); *G06T 2207/30204* (2013.01)

(58) Field of Classification Search
None
See application file for complete search history.

(56) References Cited

U.S. PATENT DOCUMENTS

| | | | |
|---|---|---|---|
| 9,974,521 B2 | 5/2018 | Hancu et al. | |
| 10,398,397 B2 | 9/2019 | Muller et al. | |
| 2012/0134464 A1 | 5/2012 | Hoernig et al. | |
| 2016/0235380 A1* | 8/2016 | Smith | A61B 6/0414 |
| 2018/0078230 A1 | 3/2018 | Hoernig | |
| 2020/0100750 A1 | 4/2020 | Mertelmeier et al. | |
| 2020/0129740 A1* | 4/2020 | Kottenstette | A61B 5/6852 |

OTHER PUBLICATIONS

EP application 21156134.5 filed Feb. 9, 2021—Extended Search Report dated Jul. 26, 2021; 9 pages.

* cited by examiner

*Primary Examiner* — Hoon K Song
(74) *Attorney, Agent, or Firm* — McCoy Russell LLP

(57) ABSTRACT

Various methods and systems are provided for tracking a biopsy target across one or more images. In one example, a method includes determining a position of a biopsy target in a selected image of a patient based on an image registration process with a reference image of the patient, and displaying a graphical representation of the position of the biopsy target on the selected image.

18 Claims, 9 Drawing Sheets

METHODS AND SYSTEMS FOR DIGITAL MAMMOGRAPHY IMAGING

FIELD

Embodiments of the subject matter disclosed herein relate to digital mammography imaging procedures.

BACKGROUND

Mammography is a medical imaging procedure for detecting one or more tumors of a breast. Based on mammography imaging, a breast biopsy procedure may be performed to obtain a biopsy sample of the concerned breast tissue for further analysis. During a breast biopsy procedure, the breast is compressed with a compression paddle, and is positioned in either a mediolateral or craniocaudal position, depending on whether the biopsy is performed in a horizontal approach, where the needle is inserted into the tissue along a mediolateral plane parallel to the detector, or a vertical approach, where the needle is inserted vertically along a craniocaudal plane. Location of a target tissue (e.g., lesion, microcalcification, etc.) is then identified based on a mammography imaging procedure, such as digital breast tomosynthesis (DBT). For example, during DBT, a scout image (where x-ray tube is in a midline position perpendicular to the detector) and a plurality of stereo images (where the x-ray tube moves in an arc at various angles within a set degree from the midline in both the positive and negative directions) are obtained. The target location within a region of interest (ROI) may be selected based on the acquired images. Upon selecting the target, a needle is inserted into the breast using a biopsy tool, and a portion of the target tissue is excised with the needle to obtain the biopsy sample.

BRIEF DESCRIPTION

In one embodiment, a method includes determining a position of a biopsy target in a selected image of a patient based on an image registration process with a reference image of the patient, and displaying a graphical representation of the position of the biopsy target on the selected image.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below.

DETAILED DESCRIPTION

Figure 1:
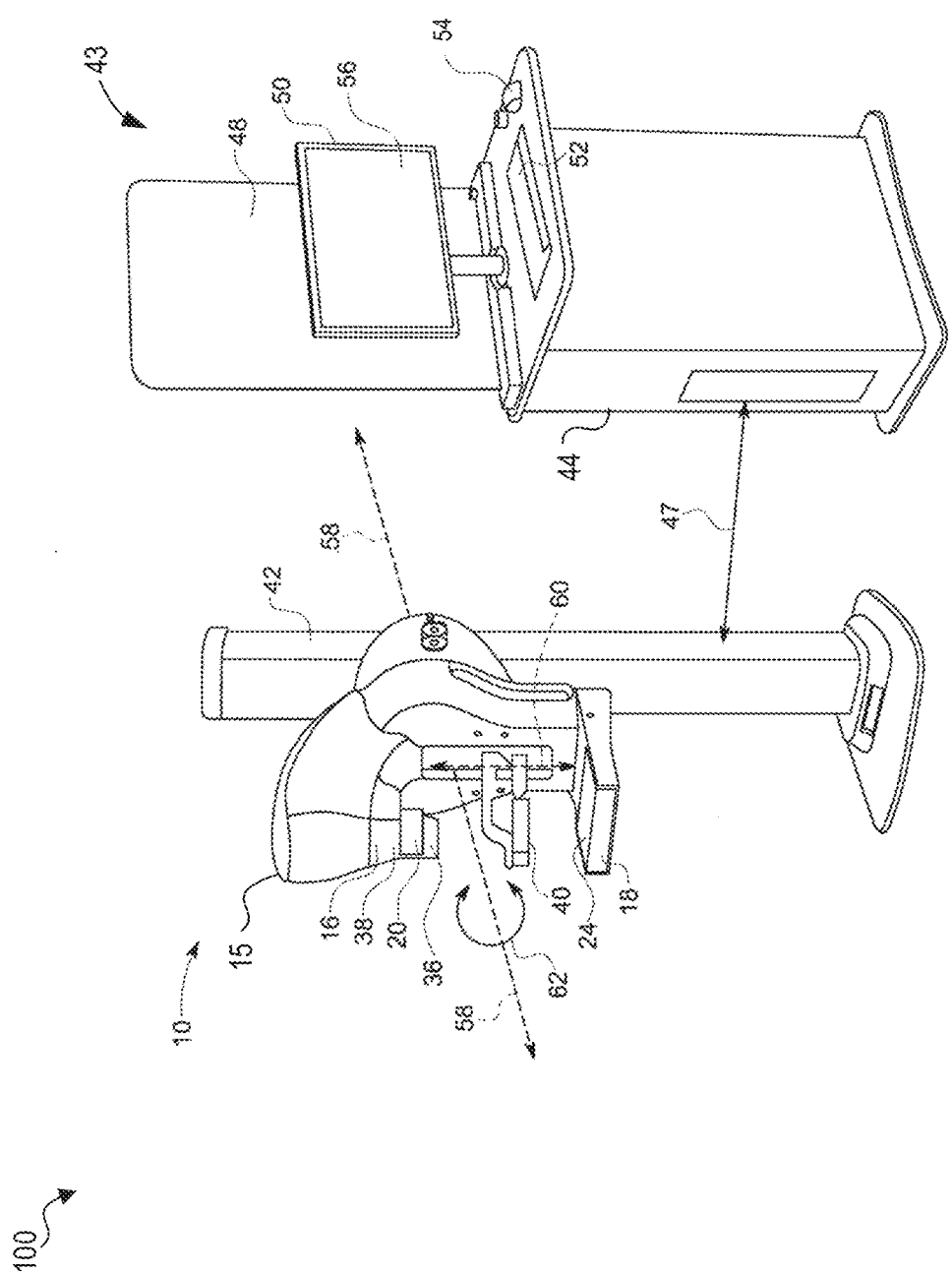
FIG. 1 is a schematic illustration of a digital mammography system according to an embodiment.

The following description relates to various embodiments for digital mammography imaging procedures. Digital mammography imaging procedures may include acquiring 2-dimensional (2D) or 3D digital images of the breast. For example, DBT is an imaging technique for generating cross-sectional images of a breast at high in-plane resolution. During imaging using a digital mammography system, the breast is compressed and an x-ray source may be rotated around the breast within a range of angles in positive and negative directions from a medial position. Low dose x-ray projection images of the breast at each angle may be obtained at a detector. The projection images are then reconstructed as slice images of breast volume along the z-direction.

Some medical procedures, such as breast biopsies, may be carried out with assistance from contrast-enhanced imaging performed with a digital mammography system. Contrast-enhanced imaging includes the administration of a contrast agent, such as iodine, to an imaging subject (e.g., patient). The contrast agent may travel to the patient's vasculature, which may assist in biopsy target (e.g., lesion) visualization. Following administration of the contrast agent, dual energy images may be obtained at various points of the biopsy procedure, such as immediately after contrast agent injection and prior to anesthesia delivery, after anesthesia delivery, after biopsy needle insertion, after firing of the biopsy device, after sample collection, and/or after biopsy clip insertion. A dual energy image may be generated from two images, where the two images include a first image acquired with low radiation energy (termed a low energy image, or LE) and a second image acquired with high radiation energy (termed a high energy image, or HE). A digital subtraction process may be used to generate the dual energy (DE) image from the LE image and the HE image, such that background features are removed from the DE image and the contrast-enhanced features (e.g., the lesion) are better visualized.

In some examples, the biopsy target (e.g., lesion) may no longer be visible at a given moment of the procedure due to contrast agent washout. Other imaging techniques relying on morphological information (e.g. 2D or 3D non-contrast enhanced images) will in this case be used during the remainder of the procedure. However, in some examples, the biopsy target morphology may not be clearly visible on non-contrast-enhanced images, which may prevent the biopsy procedure from continuing.

Thus, according the embodiments disclosed herein, a user may define a marker (or pixel position) of the biopsy target in any given reference image where the contrast agent is still present and image registration may be applied to recalculate the position of the biopsy target in any subsequent morphological 2D image or 3D reconstructed slice. The registered biopsy target position, or a previously calculated biopsy target contour, are therefore highlighted on all subsequent morphological images, allowing the procedure to continue with increased confidence.

Figure 2:
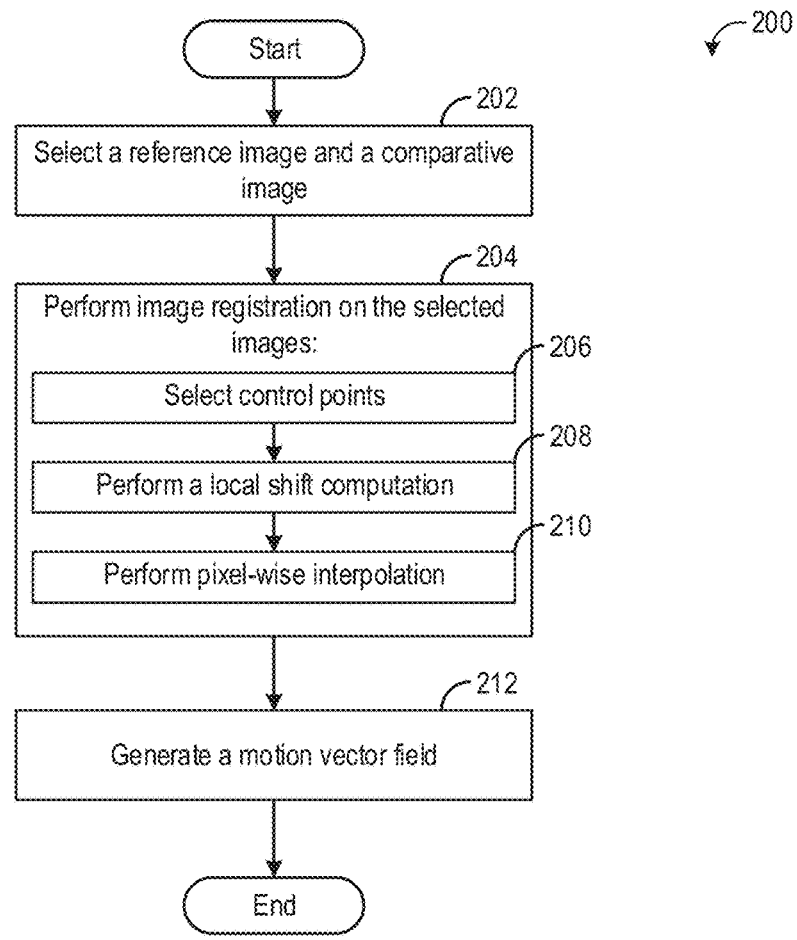
FIG. 2 is an image registration method according to an embodiment.
Figure 3:
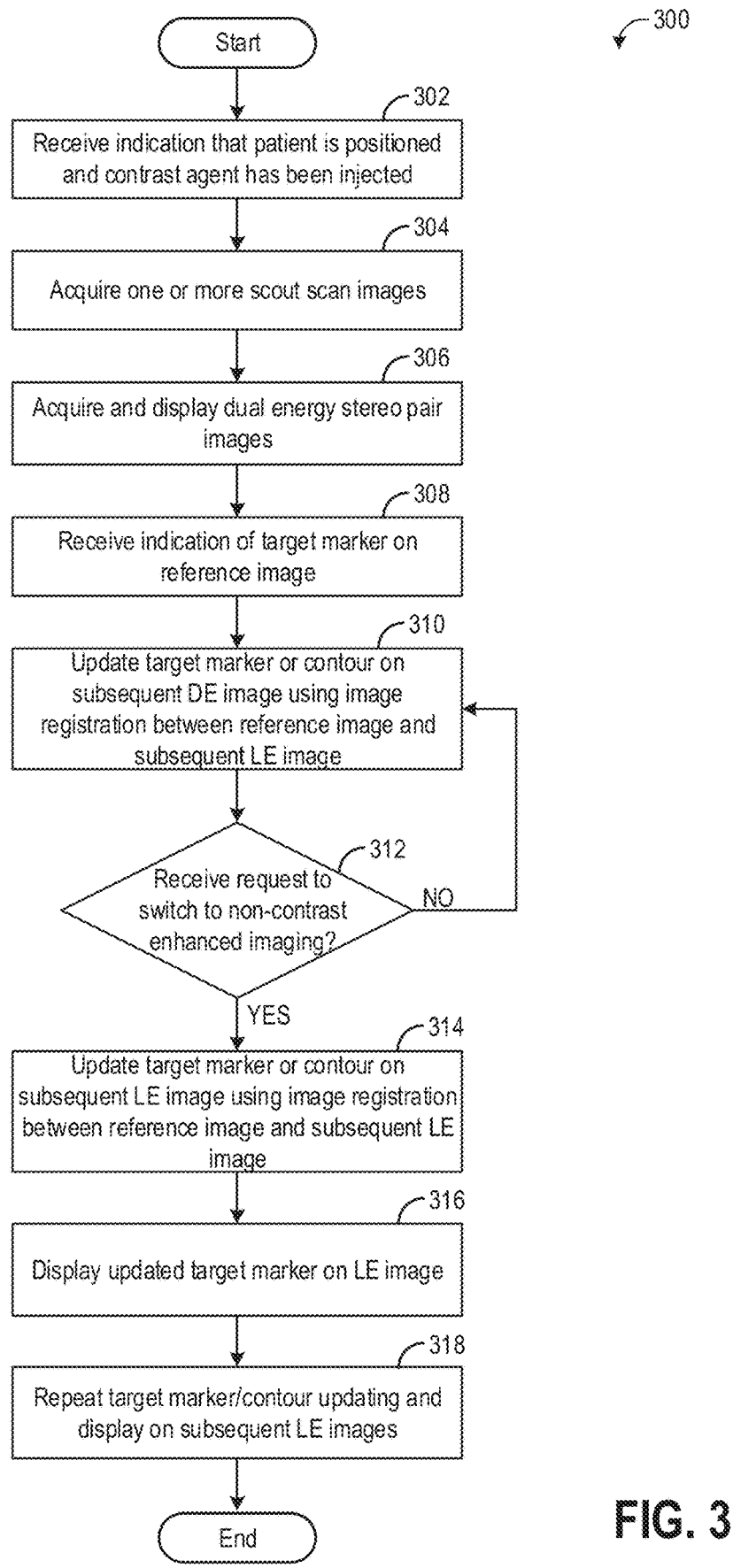
FIG. 3 is a flow chart of a method for tracking a target marker or region of interest across one or more images, according to embodiments disclosed herein.
Figure 4:
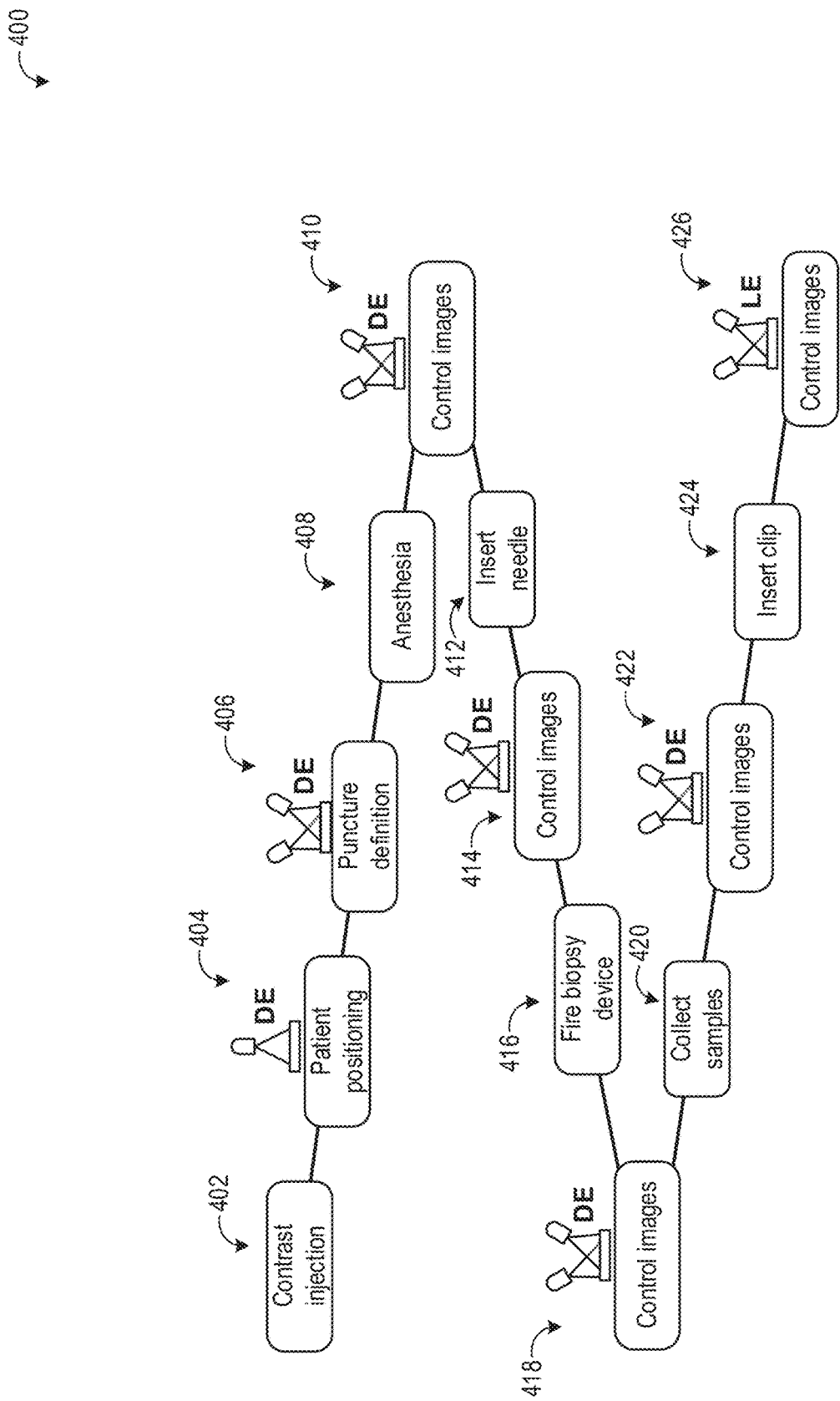
FIG. 4 schematically shows a process for performing a biopsy assisted with contrast-enhanced imaging.
Figure 5:
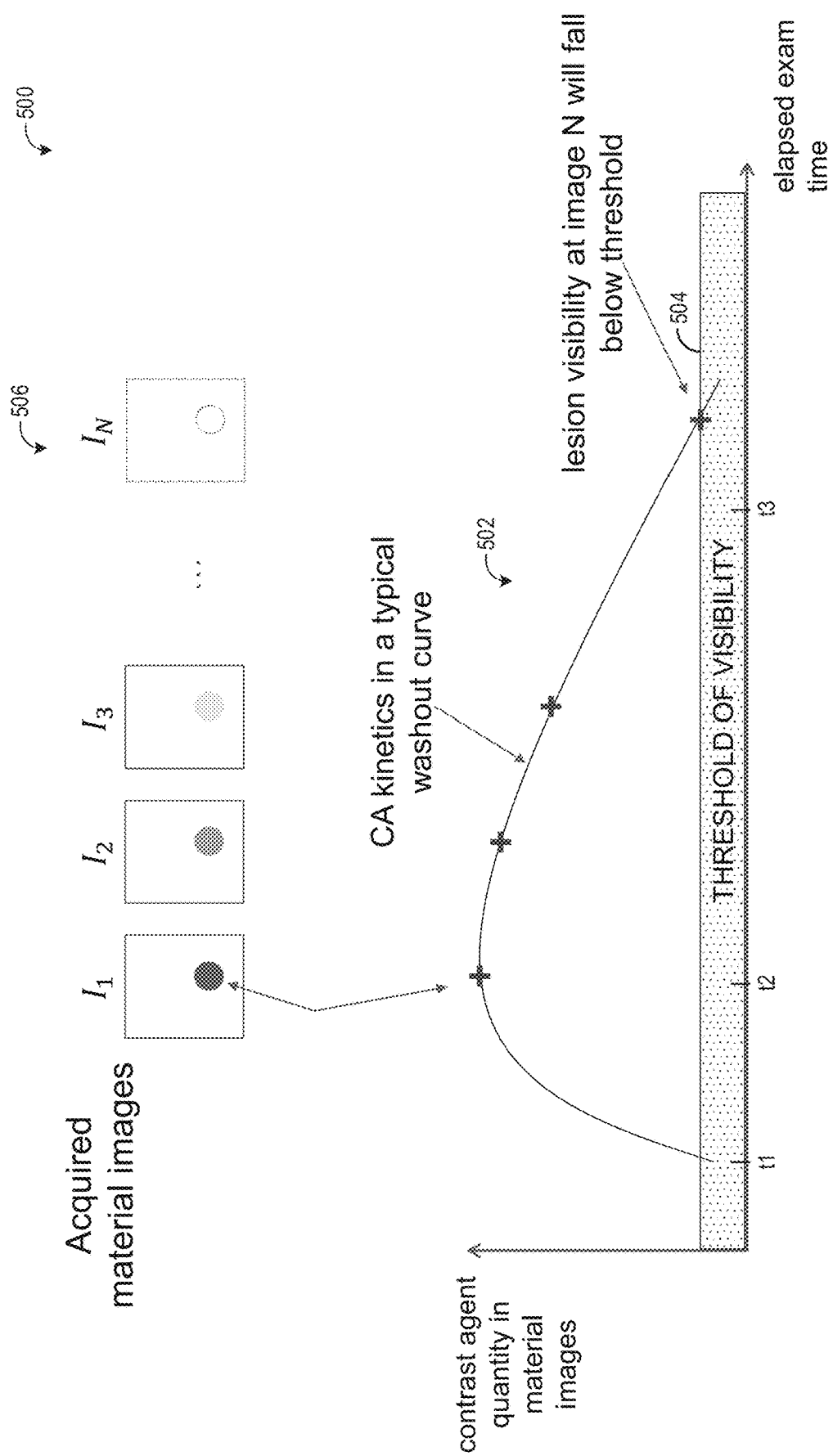
FIG. 5 schematically shows an example contrast agent washout curve.
Figure 6:
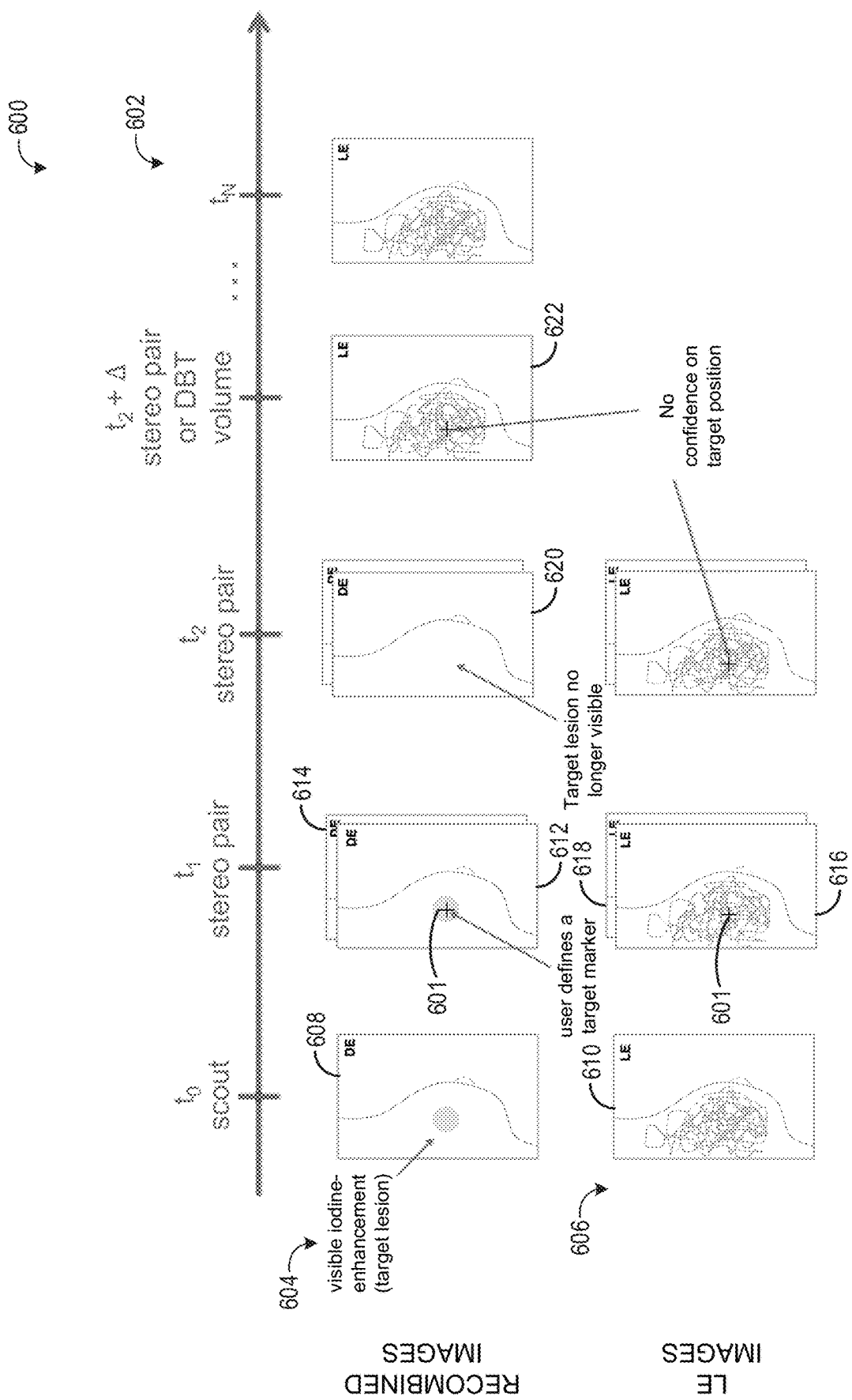
FIG. 6 schematically shows an example timeline for contrast enhanced imaging during a biopsy procedure.
Figure 7:
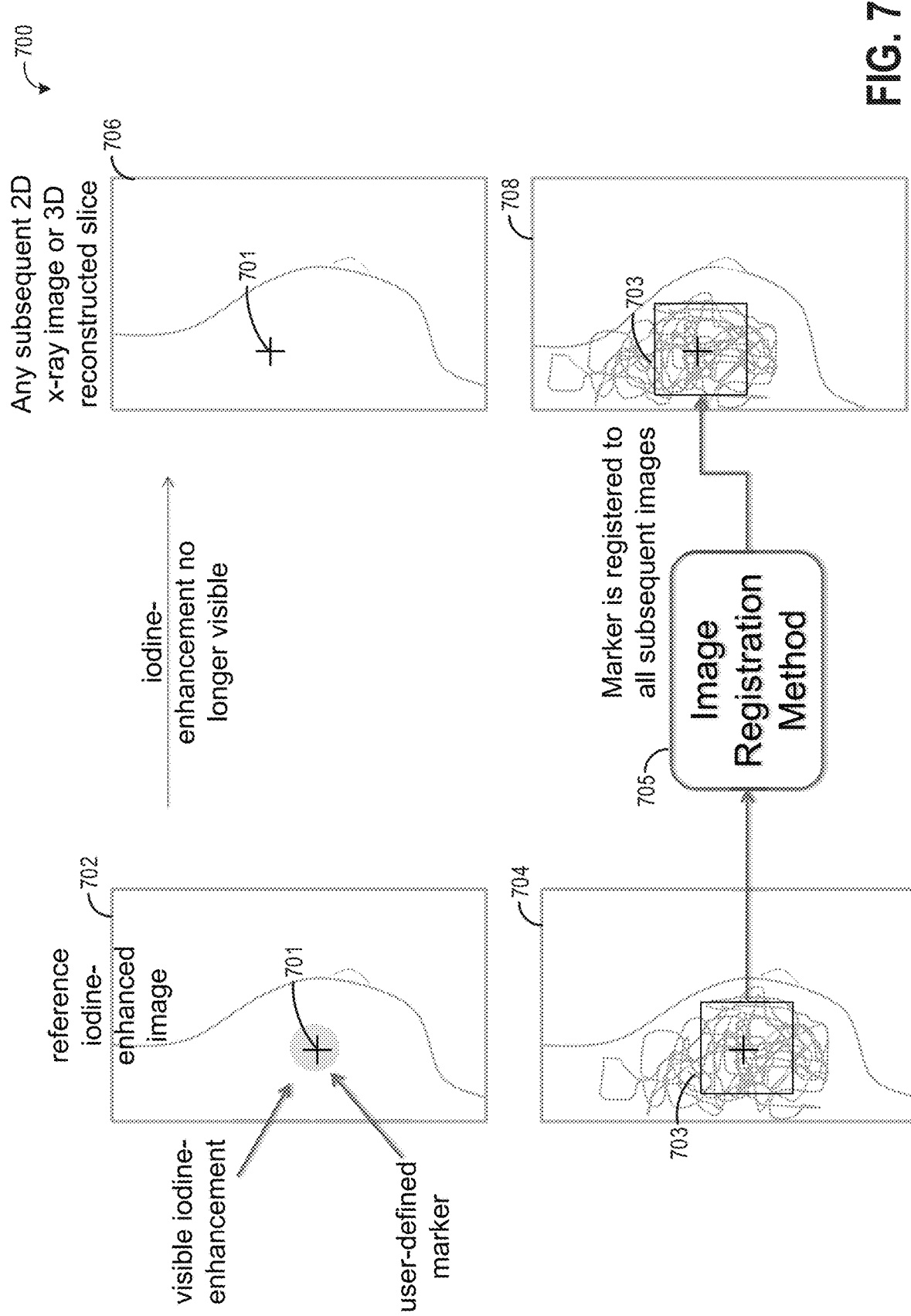
FIG. 7 schematically shows an example procedure for tracking a target marker across two images, according to an embodiment.
Figure 8:
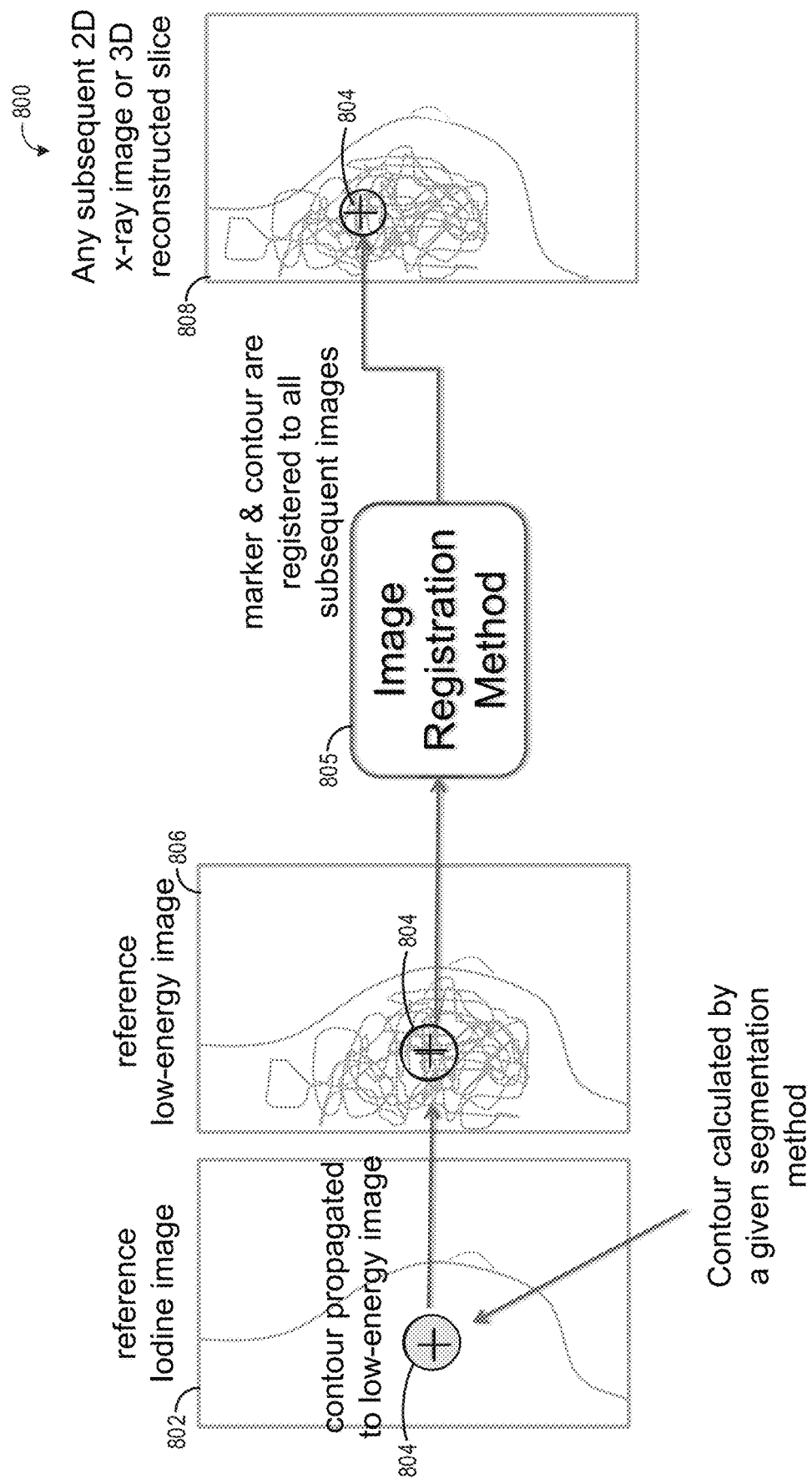
FIG. 8 schematically shows an example procedure for tracking a target ROI contour across two images, according to an embodiment.

FIG. 1 is a schematic illustration of a digital mammography system that may be used to acquire contrast-enhanced images during a biopsy procedure, such as the biopsy procedure schematically illustrated in FIG. 4. FIG. 2 is an image registration method that may be applied to generate dual energy images via the digital mammography system, as shown schematically at FIG. 9. FIG. 3 is a flow chart of a method for tracking a biopsy target across one or more images. FIG. 5 schematically shows an example contrast agent washout curve and how biopsy target visualization may decrease as the contrast agent washes out. FIG. 6 shows an example timeline for contrast-enhanced imaging during a biopsy procedure, including a time point where the biopsy target is no longer visible due to contrast agent washout. FIGS. 7 and 8 show example processes for target marker/contour tracking using image registration.

Referring to FIG. 1, a digital mammography system 100 including an x-ray system 10 for performing a mammography procedure is shown, according to an embodiment of the disclosure. The x-ray system 10 may be a tomosynthesis system, such as a digital breast tomosynthesis (DBT) system. Further, the x-ray system 10 may be used to perform one or more procedures including digital tomosynthesis imaging, and DBT guided breast biopsy.

The x-ray system 10 includes a support structure 42, to which a radiation source 16, a radiation detector 18, and a collimator 20 are attached. The radiation source 16 is housed within a gantry 15 that is movably coupled to the support structure 42. In particular, the gantry 15 may be mounted to the support structure 42 such that the gantry 15 including the radiation source 16 can rotate around an axis 58 in relation to the radiation detector 18. An angular range of rotation of the gantry 15 housing the radiation source 16 indicates a rotation up to a desired degree in either direction about the axis 58. For example, the angular range of rotation of the radiation source 16 may be $-\theta$ to $+\theta$, where $\theta$ may be such that the angular range is a limited angle range, less than 360 degrees. An exemplary x-ray system may have an angular range of ±11 degrees, which may allow rotation of the gantry (that is rotation of the radiation source) from −11 degrees to +11 degrees about an axis of rotation of the gantry. The angular range may vary depending on the manufacturing specifications. For example, the angular range for DBT systems may be approximately ±11 degrees to ±60 degrees, depending on the manufacturing specifications.

The radiation source 16 is directed toward a volume or object to be imaged and is configured to emit radiation rays at desired times to acquire one or more images. The radiation detector 18 is configured to receive the radiation rays via a surface 24. The detector 18 may be any one of a variety of different detectors, such as an x-ray detector, digital radiography detector, or flat panel detector. The collimator 20 is disposed adjacent to the radiation source 16 and is configured to adjust an irradiated zone of a subject.

In some embodiments, the system 10 may further include a patient shield 36 mounted to the radiation source 16 via face shield rails 38 such that a patient's body part (e.g., head) is not directly under the radiation. The system 10 may further include a compression paddle 40, which may be movable upward and downward in relation to the support structure along a vertical axis 60. Thus, the compression paddle 40 may be adjusted to be positioned closer to the radiation detector 18 by moving the compression paddle 40 downward toward the detector 18, and a distance between the detector 18 and the compression paddle 40 may be increased by moving the compression paddle upward along the vertical axis 60 away from the detector. The movement of the compression paddle 40 may be adjusted by a user via compression paddle actuator (not shown) included in the x-ray system 10. The compression paddle 40 may hold a body part, such as a breast, in place against the surface 24 of the radiation detector 18. The compression paddle 40 may compress the body part and hold the body part still in place while optionally providing apertures to allow for insertion of a biopsy needle, such as a core needle or a vacuum assisted core needle. In this way, compression paddle 40 may be utilized to compress the body part to minimize the thickness traversed by the x-rays and to help reduce movement of the body part due to the patient moving. The x-ray system 10 may also include an object support (not shown) on which the body part may be positioned.

The digital mammography system 100 may further include workstation 43 comprising a controller 44 including at least one processor and a memory. The controller 44 may be communicatively coupled to one or more components of the x-ray system 10 including one or more of the radiation source 16, radiation detector 18, the compression paddle 40, and a biopsy device. In an embodiment, the communication between the controller and the x-ray system 10 may be via a wireless communication system. In other embodiments, the controller 44 may be in electrical communication with the one or more components of the x-ray system via a cable 47. Further, in an exemplary embodiment, as shown in FIG. 1, the controller 44 is integrated into workstation 43. In other embodiments, the controller 44 may be integrated into one or more of the various components of the system 10 disclosed above. Further, the controller 44 may include processing circuitry that executes stored program logic and may be any one of a different computers, processors, controllers, or combination thereof that are available for and compatible with the various types of equipment and devices used in the x-ray system 10.

The workstation 43 may include a radiation shield 48 that protects an operator of the system 10 from the radiation rays emitted by the radiation source 16. The workstation 43 may further include a display 50, a keyboard 52, mouse 54, and/or other appropriate user input devices that facilitate control of the system 10 via a user interface 56.

Controller 44 may adjust the operation and function of the x-ray system 10. As an example, the controller 44 may provide timing control, as to when the x-ray source 16 emits x-rays, and may further adjust how the detector 18 reads and conveys information or signals after the x-rays hit the detector 18, and how the x-ray source 16 and the detector 18 move relative to one another and relative to the body part being imaged. The controller 44 may also control how information, including images 42 and data acquired during the operation, is processed, displayed, stored, and manipulated. Various processing steps as described herein with respect to FIGS. 2 and 3, performed by the controller 44, may be provided by a set of instructions stored in non-transitory memory of controller 44.

Further, as stated above, the radiation detector 18 receives the radiation rays 22 emitted by the radiation source 16. In particular, during imaging with the x-ray system, a projection image of the imaging body part may be obtained at the detector 18. In some embodiments, data, such as projection image data, received by the radiation detector 18 may be electrically and/or wirelessly communicated to the controller 44 from the radiation detector 18. The controller 44 may then reconstruct one or more scan images based on the projection image data, by implementing a reconstruction algorithm, for example. The reconstructed image may be displayed to the user on the user interface 50 via a display screen 56.

The radiation source 16, along with the radiation detector 18, forms part of the x-ray system 10 which provides x-ray imagery for the purpose of one or more of screening for abnormalities, diagnosis, dynamic imaging, and image-guided biopsy. For example, the x-ray system 10 may be operated in a mammography mode for screening for abnormalities. During mammography, a patient's breast is positioned and compressed between the detector 18 and the compression paddle 40. Thus, a volume of the x-ray system 10 between the compression paddle 40 and the detector 18 is an imaging volume. The radiation source 16 then emits radiation rays on to the compressed breast, and a projection image of the breast is formed on the detector 18. The projection image may then be reconstructed by the controller 44, and displayed on the interface 50. During mammography, the gantry 15 may be adjusted at different angles to obtain images at different orientations, such as a cranio-caudal (CC) image and a medio-lateral oblique (MLO) image. In one example, the gantry 15 may be rotated about the axis 58 while the compression paddle 40 and the detector 18 remain stationary. In other examples, the gantry 15, the compression paddle 40, and the detector 18 may be rotated as a single unit about the axis 58.

Further, the x-ray system 10 may be operated in a tomosynthesis mode for performing digital breast tomosynthesis (DBT). During tomosynthesis, the x-ray system 10 may be operated to direct low-dose radiation towards the imaging volume (between the compression paddle 40 and the detector 18) at various angles over the angular range of the x-ray system 10. Specifically, during tomosynthesis, similar to mammography, the breast is compressed between the compression paddle 40 and the detector 18. The radiation source 16 is then rotated from $-\theta$ to $+\theta$, and a plurality of projection images of the compressed breast is obtained at regular angular intervals over the angular range. For example, if the angular range of the x-ray system is $\pm 11$ degrees, 22 projection images may be captured by the detector during an angular sweep of the gantry at approximately one every one degree. The plurality of projection images are then processed by the controller 44 to generate a plurality of DBT image slices. The processing may include applying one or more reconstruction algorithms to reconstruct three dimensional image of the breast. Furthermore, the x-ray system may be configured to perform a DBT-guided biopsy procedure. Accordingly, in some exemplary embodiments, the system 10 may further include a biopsy device comprising a biopsy needle for extracting a tissue sample for further analysis.

In some examples, digital mammography system 100 may be configured to perform contrast imaging where contrast agents, such as iodine, can be injected into the patient that travel to the region of interest (ROI) within the breast (e.g., a lesion). The contrast agents are taken up in the blood vessels surrounding a cancerous lesion in the ROI, thereby providing a contrasting image for a period of time with respect to the surrounding tissue, enhancing the ability to locate the lesion.

The use of a contrast agent can be coupled with images of the ROI taken using dual-energy imaging processes and technology. In dual-energy imaging, low-energy (LE) and high-energy (HE) images are taken of the ROT. In particular, contrast enhanced spectral mammography (CESM) (2D) and contrast enhanced digital breast tomosynthesis (CE-DBT) (3D) imaging modalities are performed with dual-energy technology. For each view (single view in CESM, multiple views for CE-DBT), a pair of images is acquired: a low-energy (LE) image and a high-energy (HE) image. In CE-DBT, non-paired HE and LE images may be acquired for each view and an HE volume, LE volume, and recombined CE volumes may be reconstructed for the ROT. For example, the HE and LE views may be interleaved during the CE-DBT scan (alternatively HE, LE, HE, LE, HE, LE, etc.) with a switch from HE to LE then to HE again etc., for each angulated position of the x-ray tube. The LE and HE images are usually obtained at mean energies above and below the k-edge of the contrast agent. At x-ray energies just above the k-edge of the contrast agent, the absorption of x-rays is increased resulting in an increase of contrast from the iodine contrast agent in the HE image.

In dual-energy 3D or stereotactic procedures, LE and HE image acquisitions are performed, with at least two different positions of the x-ray source with respect to the detector. The images are then recombined to display material-specific information with regard to the internal structure of the tissue being imaged. In the case of 3D CESM, for example, after the injection of contrast medium, dual-energy images are acquired at two or more positions of the x-ray tube with respect to the detector. For each of these tube angulations, the low and high-energy images are recombined to produce an image of the contrast medium surface concentration at each pixel to provide an iodine-equivalent or dual-energy (DE) image(s) (for a single view in CESM, and for multiple views for CE-DBT), which in CE-DBT, are used to reconstruct a 3D volume. Image recombination may be performed based on simulations of the x-ray image chain, via calibrations on a reference phantom, or any other suitable 3D-reconstruction process. Additionally, in the continuous mode of acquisition where the x-ray tube moves continuously with interleaved HE and LE images being taken, the LE images are used to reconstruct a LE 3D volume, and the HE images are used to reconstruct a HE 3D volume, with both volumes being recombined in a suitable manner to provide an iodine 3D volume. In some examples, 3D-reconstruction and HE/LE recombination may be performed in a single step.

FIG. 2 is an image registration method 200 that may be applied to images acquired by a digital mammography system (e.g. digital mammography system 100 of FIG. 1) to compare or integrate data obtained within different images from an image set. In some examples, image registration may be used as a preliminary step in other image processing applications, such as to track a biopsy target (see FIG. 3). Method 200 may be executed using computer readable instructions stored in the non-transitory memory of a computing device of a digital mammography system (e.g., digital mammography system 100 of FIG. 1) or a controller communicatively coupled to the digital mammography system (e.g., controller 44 of FIG. 1). In some embodiments, method 200 may be executed by another computing device without departing from the scope of this disclosure (e.g., an edge device, a picture archiving and communication system (PACS)).

At 202, a reference image and a comparative image may be selected from an image set acquired by the digital mammography system. In some examples, more than one comparative image may be selected. The reference image herein may be defined as the image to which the comparative image (or images) is aligned during image registration. The reference image may be a low energy image and the comparative image may be a high energy image, in some examples. In other examples (such as when the image registration method is performed to track a biopsy target according to the method of FIG. 3), the reference image may be a low energy image during a point in time when the biopsy target was still visible in contrast-enhanced images and the comparative image may be low energy image taken at a time subsequent to the reference image, at a point in time when the biopsy target was no longer visible in contrast-enhanced images and thus the user of the digital mammography system had switched to non-contrast imaging. The reference image and the comparative image may be images of the same anatomical features/scan plane of the same patient.

At 204, image registration may be performed on the selected images. During image registration, the comparative image may be aligned to the reference image via a spatial domain method. The spatial domain method may include selecting control points within the reference image and the comparative image at 206. The control points may be individual pixels or groups of neighboring pixels. The control points may be selected randomly in one example. In another example, the control points may be selected based on a predefined grid or other pattern. In a still further example, the control points may be selected based on which pixels/anatomical regions of the comparative image are likely to move from image to image, such as pixels at edges of anatomical structures. The control points may be at the same location in each of the reference image and the comparative image.

At 208, a local shift computation may be performed between the control points of the two images. The local shift computation may indicate, for each control point of the comparative image, the magnitude and direction of shift of that control point relative to the reference image. For example, the local shift computation may generate a motion vector that comprises the vector difference between the position x,y (for rows and columns) of the same clinical/anatomical feature (e.g., a micro calcification or a lesion) in the two images: dx=x1−x2, dy=y1−y2.

At 210, pixel-wise interpolation may be performed based on the local shift computation. The interpolation may include a first interpolation that is performed to pass from the motion vectors at each control point to a motion vector field with motion vectors at every image pixel (e.g., the pixel wise interpolation 909 in FIG. 9). The first interpolation may include B-spline interpolation or another suitable interpolation. Thus, the first interpolation may include a B-spline interpolation to generate a motion vector field, as indicated 212, where the motion vector field includes a respective motion vector at every pixel based on the motion vectors at the control points. A second interpolation may be performed where, for every pixel p (xp, yp) in the comparative image (e.g., the image that is being registered), the vector field value at pixel p (dx,dy) is used to retrieve the image pixel value in position (xp+dx, yp+dy) in the same image (because that is where the pixel is supposed to be, according to the reference image). Since dx and dy are not integer values, interpolation is performed on the surrounding pixels using a linear or cubic function, for example, which may create a registered image as explained below.

FIG. 3 is a flow chart of a method 300 for tracking a biopsy target across one or more images. Method 300 may be executed using computer readable instructions stored in the non-transitory memory of a computing device of a digital mammography system (e.g., digital mammography system 100 of FIG. 1) or a controller communicatively coupled to the digital mammography system (e.g., controller 44 of FIG. 1). In some embodiments, method 300 may be executed by another computing device without departing from the scope of this disclosure (e.g., an edge device, a picture archiving and communication system (PACS)).

At 302, an indication is received that a patient/biopsy subject has been positioned and that a contrast agent has been injected in the patient. The indication may be received via user input (e.g., an operator of the digital mammography system may enter a user input via a touch screen, keyboard, etc., indicating that contrast agent has been injected) and/or via commands/sensor input from the digital mammography system (e.g., the contrast agent may be injected via an automatic system that notifies the digital mammography system when contrast agent injection has commenced). In some examples, the indication that the patient is positioned and that the contrast agent has been injected/administered may be implied based on a user request to commence imaging. The contrast agent may be iodine or another suitable contrast agent.

At 304, one or more scout scan images are acquired. The scout scan images may be obtained with the x-ray source in a single/fixed position (e.g., a medial position, obtained with the x-ray tube positioned at zero degrees from a midline axis perpendicular to the top surface of the detector). The scout scan images may be lose dose, short exposure images. In some examples, a brightness of the scout scan image may be assessed to determine the x-ray technique (e.g., x-ray source current and voltage) for subsequent images. The scout scan images may be single energy images (e.g., low energy images) or dual energy subtraction images (e.g., where a low energy image and a high energy image are obtained, registered, and then one image is subtracted from the other to remove background and highlight the contrast agent).

At 306, a plurality of dual energy stereo pair images are acquired and displayed (e.g., on display screen 56) over the course of the biopsy procedure. The dual energy stereo pair images may include a first dual energy image generated from LE and HE image acquisitions at a first position of the x-ray source with respect to the detector (e.g., −11°) and a second dual energy image generated from LE and HE image acquisitions at a second position of the x-ray source with respect to the detector (e.g., 11°). In some examples, LE and HE acquisitions may be performed for each dual energy image. In other examples, at least some dual energy images may be generated from prior LE or HE acquisitions. For example, a current HE image may be recombined with a prior LE image (e.g., used to generate an earlier dual energy image).

The dual energy stereo pair images may be acquired at various stages of the biopsy procedure when requested by the operator of the digital mammography system. FIG. 4 shows an example sequence 400 for a contrast image-guided biopsy procedure, which illustrates exemplary time points when dual energy stereo pair images may be obtained. The sequence commences with contrast injection at 402, where a contrast agent such as iodine is injected to the biopsy subject (e.g., a patient). At 404, following contrast injection, one or more scout images may be obtained for patient positioning purposes. Once it is confirmed that the patient is properly positioned, dual energy (DE) stereo pair images are obtained at 406 to define the position of the biopsy target (e.g., a lesion). Once the biopsy target has been identified and its position determined, local anesthesia may be delivered at 408. In some examples, additional dual energy stereo pair images (referred to as control images) may be acquired at 410, after delivery of the anesthesia. However, in other examples, the additional image acquisition at 410 may be dispensed with.

At 412, the biopsy needle is inserted and moved to the biopsy target. To visualize the biopsy needle as the biopsy needle is positioned to a target position relative to the biopsy target, further control images are obtained at 414. As explained above, these control images are dual energy stereo pair images, and multiple rounds of dual energy stereo pair images may be acquired in order to visualize the needle relative to the biopsy target as the needle is moved.

Once the biopsy needle is a target position, the biopsy device is fired at 416, which results in puncture of the biopsy target and eventually collection of biopsy samples at 420. During the process of the firing of the biopsy device and sample collection, additional control images may be acquired, as shown at 418. After sample collection, control images may be acquired at 422. A biopsy clip is inserted at 424, and further control images may be acquired at 426. The control images acquired at 422 and 426 may assist a clinician performing/overseeing the biopsy procedure in ensuring the biopsy was properly performed and the clip positioned correctly. The control images acquired at 426 may be low energy images rather than dual energy images, as the visualization of the biopsy target is no longer necessary.

Thus, during the biopsy procedure, dual energy images are acquired and displayed in order to assist in positioning the biopsy needle and ensure the biopsy procedure is performed properly. Each dual energy image is generated from a low energy image and a high energy image and results in enhanced visualization of the contrast agent. Without the contrast agent, some biopsy targets, such as lesions, may be difficult to visualize. As appreciated from the example sequence 400 shown in FIG. 4 and explained above, a typical biopsy procedure includes multiple steps, with dual energy images acquired at/between the steps. Some steps, such as the positioning of the biopsy needle, may be relatively time-consuming. As a result, the overall procedure may be lengthy, e.g., 20-30 minutes. Typical contrast agents, such as iodine, do not persist in the patient for very long, and in some examples may washout before the biopsy procedure has been completed.

FIG. 5 schematically shows an example of contrast agent kinetics 500, including a contrast agent curve 502 illustrating contrast agent quantity (as measured in acquired images) as a function of time during an example biopsy procedure. Included as part of the contrast agent curve 502 is a threshold of visibility 504. When the contrast agent quantity is within the threshold of visibility, the contrast agent quantity within a biopsy target (e.g., lesion) may be too low to be seen on the acquired dual energy images.

Contrast agent curve 502 may commence at injection of the contrast agent at time t1 and increase to a peak quantity at time t2. After the peak, the contrast agent quantity may gradually decrease until the contrast agent quantity reaches the threshold of visibility 504 at time t3. Dual energy images may be acquired over the course of the biopsy procedure (also referred to herein as an exam), such as the plurality of images 506 shown in FIG. 5. The plurality of images 506 may include a first image ($I_1$), a second image ($I_2$), a third image ($I_3$), and so forth, on up to an Nth image ($I_N$). The first image may be acquired near the peak of the contrast agent quantity, and thus the biopsy target (shown as a dot in the first image) may be highly visible relative to the background of the first image. As the contrast agent quantity decreases, the visibility of the biopsy target also decreases. As shown in FIG. 5, the Nth image is acquired at time t3, when the contrast agent quantity has decreased to or below the threshold of visibility 504. As a result, the biopsy target is no longer visible. Without the ability to visualize the biopsy target via the contrast agent, imaging of the biopsy target may be switched to non-contrast enhanced imaging (e.g., low energy stereo pair images), which may rely on morphological information rather than contrast agent visibility to visualize the biopsy target. However, in some examples, the biopsy target may not be sufficiently visible on the non-contrast enhanced images, which may result in the biopsy procedure being stopped altogether. Thus, patient care may be negatively impacted if contrast agent washout occurs before the biopsy procedure is complete.

Thus, the location of the biopsy target may be identified by a user (e.g., a clinician performing or assisting with the biopsy procedure) in a displayed dual energy image or other suitable displayed image. Once the biopsy target location has been identified, the biopsy target may be tracked across each subsequent image using the image registration process described above with respect to FIG. 2. If the contrast agent washes out and the biopsy target is no longer sufficiently visible, a representation of the biopsy target (e.g., a box, circle, dot, etc.) may be superimposed on subsequent images (e.g., non-contrast enhanced images), at the position of the biopsy target as determined from the image registration process. In doing so, the position of the biopsy target may be tracked and then visualized when requested, which may allow the biopsy procedure to continue even after contrast agent washout.

Returning to FIG. 3, an indication of a target marker on a reference image may be received, as indicated at 308. The reference image may be a low energy image used to generate a dual energy image in which the biopsy target is sufficiently visible. The target marker may indicate the location of the biopsy target within the reference image. The target marker may be a box, circle, dot, or another marker that selects a region of interest (e.g., a group of pixels) as being the biopsy target and may be determined from user input entered to the dual energy image via a touch screen, a mouse, a stylus, etc. The indication of the target marker may be received at any time during the biopsy procedure, but the determination of the position of the biopsy target may be more robust and/or accurate if the indication of the target marker is received at or near peak contrast agent levels (e.g., the peak of the curve shown in FIG. 5). In some examples, once the biopsy procedure is underway, a notification may be output on a display device of/in communication with the digital mammography system (e.g., display screen 56) asking a user to enter an input indicating the location of the biopsy target. In some examples, such as when the biopsy procedure is guided with digital breast tomosynthesis, a 3D volume may be generated, and the displayed images may be reconstructed slices from the 3D volume. In some examples, a contour indicative of the border of the biopsy target may be determined using a segmentation process where the dual energy image is segmented based on the user indication of the location of the biopsy target.

At 310, the position of the target marker (or the target contour) may be updated on a subsequent dual energy (DE) image using image registration between the reference image and a subsequent low energy (LE) image. The subsequent LE image may be acquired at a later point in time than the reference image, and the subsequent LE image may be used along with an HE image to generate the subsequent DE image. For example, the reference image and the subsequent LE image may be registered according to the image registration process described above with respect to FIG. 2. When the local shift computation is performed (e.g., as explained at 208 of method 200), the amount/direction of movement of each control point in the subsequent LE image may be determined relative to each respective corresponding control point of the reference image. The two-phase pixel-wise interpolation (e.g., as explained at 210 of method 200 where a first interpolation is performed to calculate a motion vector at each pixel based on the motion vectors of the control points and a second interpolation is performed to calculate the actual shift of each pixel) may be performed based on the local shift vectors, which may result in a determination of whether and how much each pixel (or voxel) of the target marker (or target contour) has moved in the subsequent LE image relative to the reference image. As a result of the image registration, the position of the target marker in the subsequent DE image may be updated relative to the positon of the target marker in the reference image in correspondence to the movement of the pixels (or voxels) comprising the target marker determined by the image registration process. In some examples, an annotation indicating the target marker may be output as part of the subsequent DE image. In other examples, the position of the target marker may be updated, but no representation of the target marker may be visualized on the subsequent DE image.

At 312, method 300 includes determining if a request is received to switch to non-contrast enhanced imaging. As explained above, a user may opt to commence non-contrast enhanced imaging and stop contrast-enhanced imaging if the contrast agent has washed out and thus the biopsy target is no longer visualized via the contrast agent. The request may include a user input (e.g., via a touch screen, mouse, voice, control button on the digital mammography system) requesting the non-contrast enhanced imaging commence. In other examples, the request to switch to non-contrast enhanced imaging may be generated automatically by the digital mammography system, such as in response to detecting contrast agent washout (e.g., the contrast agent quantity may be determined and tracked from the dual energy images).

If a request to switch to non-contrast enhanced imaging has not been received, method 300 loops back to 310 to continue to update the position of the target marker by registering all subsequent LE images to the reference image. In some examples, the target marker may be displayed on each subsequent DE image. In other examples, the target marker may not be displayed until requested or until a switch to non-contrast-enhanced imaging is made (explained below).

If a request to switch to non-contrast enhanced imaging has been requested, method 300 proceeds to 314 to update the position of the target marker (or contour) on a subsequent LE image using image registration between the reference image and the subsequent LE image. The image registration process may be the same as described above. For example, the target marker may be registered with the position of the marker in the initial (reference) image, or the target marker may be registered with the last determined positon, such as with a most recent LE image. At 316, the updated target marker is displayed on the subsequent LE image. For example, after the subsequent LE image is acquired, the subsequent LE image may be displayed with an annotation representing the target marker (at the updated position of the biopsy target) as an overlay on the subsequent LE image. In this way, the position of the biopsy target may be visualized even during non-contrast enhanced imaging.

At 318, the updating of the target marker (or contour) via image registration and display of the target marker on subsequent LE images may be repeated until the imaging for the biopsy procedure is complete and/or until a user requests the target marker no longer be displayed. Each time the position of the target marker or contour is updated, the most-recent low energy image may be registered with the initial low energy image (e.g., which may be referred to as a reference image), where the initial low energy image is the low energy image used to generate the dual energy image in which the location of the biopsy target was first determined. In this way, multiple images may be acquired between acquisition of the initial low energy image and acquisition of an image in which the updated position of the biopsy target is determined. Method 300 then ends.

FIG. 6 schematically shows an example timeline 600 of contrast-enhanced imaging during a biopsy procedure. Timeline 600 may represent events and images that occur and are acquired during execution of method 300. The timeline 600 includes a plurality of time points 602 plotted across the top of FIG. 6, a plurality of recombined images 604 (e.g., DE images) acquired at the time points, and a plurality of LE images 606 acquired at the time points (which may be combined with HE images to generate the recombined images).

At time t0, a scout image is acquired. The scout image may be the first DE image 608 shown in FIG. 6. The first DE image 608 may be generated using a first LE image 610 and a first HE image (not shown). The recombination (e.g., digital subtraction) of the LE image and HE image results in morphological/background information being removed (e.g., the breast tissue), leaving visualization of the contrast agent, which is present in the vasculature and hence any lesions (which undergo neovascularization).

At t1, dual energy stereo pair images are acquired. The stereo pair images may include a second DE image 612 and a third DE image 614. The second DE image 612 may be the product of recombination of a second LE image 616 and a second HE image (not shown) and the third DE image 614 may be the product of recombination of a third LE image 618 and a third HE image (not shown). The second LE image and second HE image may be acquired with the x-ray source of the digital mammography system at a first position, and the third LE image and third HE image may be acquired with the x-ray source of the digital mammography system at a second position, different than the first position.

A user may define a target marker 601 at time t1, in the second DE image 612. Because the second DE image is the result of recombination of the second LE image 616 and the second HE image, the position of the target marker is also defined in the second LE image 616.

At time t2, additional dual energy stereo pair images are acquired, such as fourth DE image 620. However, due to contrast agent washout, the lesion is no longer visible. The user of the digital mammography system may switch to non-contrast enhanced imaging, resulting in display of only LE images, such as the LE image 622 acquired and displayed at time t2+Δ. Without registering the target marker to the position of the target marker in the LE image 616, the user may not have confidence in the position of the lesion in the LE images displayed after time t2. For example, the imaging of the breast tissue in the LE images may confound visualization of the lesion. However, if the target marker is registered to the target marker in the LE image 616, the positon of the target marker may be determined and displayed as part of the LE image 622, for example.

FIG. 7 schematically shows a process 700 for registering a target marker from a reference image to a subsequent non-contrast enhanced image. A reference image 702 is shown, which is a contrast-enhanced image (e.g., recombination of a LE image and an HE image, referred to as a DE image herein). A user may define a target marker 701 in the reference image 702. The target marker 701 may indicate the location of a biopsy target (e.g., lesion) in the reference image. The target marker 701 may be defined in an LE image 704 used to generate the reference image 702. In some examples, such as shown in FIG. 7, a bounding box 703 may be applied with the target marker in the center of the bounding box.

Once contrast enhancement is no longer available due to contrast agent washout, any additional images, such as image 706, may be displayed along with the target marker 701. Because the patient may move between image acquisitions, the position of the biopsy target may also move. Thus, the position of the target marker is moved if the biopsy target moves. To track movement of the biopsy target and update the position of the target marker accordingly, an image registration method 705 is performed between the LE image 704 and any/all subsequent LE images, such as LE image 708. The LE image 708 may be a subsequent LE image acquired after the LE image 704. In some examples, image 706 may be a DE image and the LE image 708 may be used to generate the DE image. In other examples, image 706 may be the LE image 708 (e.g., dual-energy imaging may be stopped and only LE images may be displayed).

The image registration method 705 may be the image registration method 200 described above with respect to FIG. 2, and thus may include selecting control points on the LE images 704, 708, determining local shift vectors between corresponding control points, and performing a pixel-wise interpolation based on the local shift vectors. The pixel-wise interpolation may provide an indication of where the bounding box 703 has moved in the LE image 708 relative to the LE image 704. By using a bounding box rather than a small, pinpoint target marker, the region that is analyzed for movement may be increased, which may increase the robustness of the determination of the position adjustment of the target marker.

FIG. 8 schematically shows a process 800 for registering a target contour from a reference image to a subsequent non-contrast enhanced image. In the process 800 shown in FIG. 8, the biopsy target may be defined by a contour rather than a pinpoint, box, or other shape unrelated to the size and shape of the biopsy target. In the process 800 shown in FIG. 8, the target marker is defined in a reference DE image 802, similar to the target marker definition described above. Once the target marker is defined, a contour 804 of the biopsy target may be calculated by a segmentation method, which may identify the borders of the biopsy target in the reference image 802. The contour 804 may be placed at the same position in a reference LE image 806 (e.g., used to generate the reference image 802).

Any subsequent 2D x-ray images or 3D reconstructed slices may include the contour, at the position of the biopsy target, which is determined by the image registration method 805 (similar to the image registration method of FIG. 2). In this way, the contour 804 may be positioned in a subsequent image 808, even after loss of contrast agent visibility.

Figure 9:
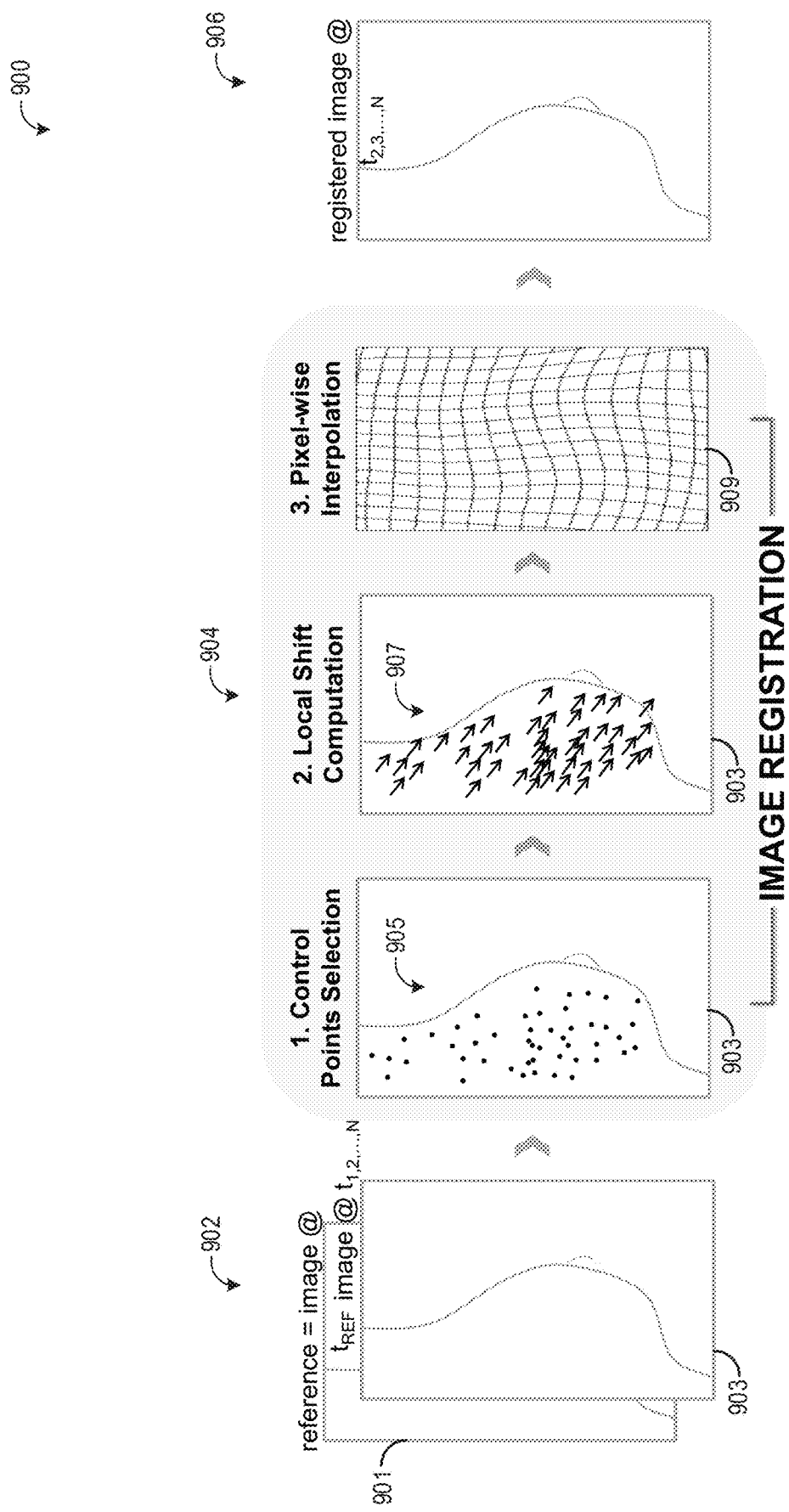
FIG. 9 schematically shows a process for image registration.

FIG. 9 schematically shows an example image registration process 900 according to an embodiment of the disclosure. The image registration process 900 shown in FIG. 9 may be carried out according to the method of FIG. 2. The image registration process 900 includes the registration of two images, shown at 902. The two images include a reference image 901 and a comparative image 903. The reference image 901 may be acquired at an earlier point in time than the comparative image 903. As explained above, the reference image may be a reference LE image acquired during peak contrast enhancement (or least when a biopsy target is sufficiently visible) while the comparative image may be an LE image acquired at any point after the reference LE image.

At 904, the two images are registered by selecting control points, computing a local shift at each control point, and performing a pixel-wise interpolation. Example control points 905 and example local shift vectors 907 are shown on comparative image 903. As appreciated by FIG. 9, the local shift computation may include determination of a vector quantifying direction and magnitude of motion/shift for each control point of the comparative image relative to the corresponding control point of the reference image. The pixels of the comparative image are then interpolated on a pixel-wise basis using an interpolation grid 909. Each pixel may be interpolated based on the pixel values of neighboring pixels and the motion vectors as described above. The output of the image registration process 900 is a registered image 906, which may in some examples be the comparative image 903 with adjustments made to some pixels in order to register (e.g., align) features of the comparative image 903 with the reference image 901. However, when tracking a biopsy target with a target marker, the output of the image registration process may include an indication of where, in the comparative image, the biopsy target is located, based on determining movement of pixels/tissue in the comparative image relative to the reference image.

Thus, the systems and methods described herein provide for enhancing visualization of a biopsy target using an image registration process. In the context of biopsy procedures guided by contrast-enhanced breast imaging, the targeted lesion may no longer be visible at a given moment of the procedure due to contrast agent washout. Other imaging techniques relying on morphological information may in this case be used during the remainder of the procedure. However, it may happen that the target lesion morphology is not clearly visible on non-contrast-enhanced images, which may prevent the biopsy procedure from continuing.

If a user defines a marker (or pixel position) in any given reference image where the contrast agent is still present, the described registration method may be used to recalculate the position of the target lesion in any subsequent morphological 2D image or 3D reconstructed slice. The registered lesion position, or a previously calculated lesion contour, are therefore highlighted on all subsequent morphological images, allowing the procedure to continue with increased confidence and reducing or avoiding aborted procedures due to contrast agent washout. A graphical representation of the target lesion, defined at a given moment to the procedure, may be displayed in all images where the lesion might be not be visible.

This may also provide for an optimized biopsy procedure workflow, relying on biopsy target/target marker tracking to increase targeting confidence and avoid aborting of the biopsy procedure. The registered lesion contour may be used to provide more accurate 3D position of the target, particularly in presence of patient motion and, as consequence, lesion displacement and deformation. In doing so, the probability of successful biopsies may be increased, patient motion may be compensated, even when contrast agent is still present, an optimized biopsy workflow may be created with decreased radiation dose and that is less time-consuming, and target accuracy may be increased by using contour information (instead of a point-based targeting).

In some examples, when 3D data is obtained, the images that are displayed during the biopsy procedure may be slices reconstructed from the 3D data. During the initial portion of the biopsy procedure, when contrast agent visualization is robust, the location and contour of the biopsy target may be tagged in the 3D volume. As imaging proceeds during the procedure, the location of the biopsy target may be tracked by image registration between newly acquired/reconstructed images and the prior 3D volume (e.g., a registration process may be performed between a 2D slice and a prior 2D slice, both of the same slice/plane of the 3D volume).

A technical effect of tracking a biopsy target using an image registration process is that registration of the target position defined at an early phase of the biopsy procedure (where the contrast agent is visible) may increase the chance of a successful biopsy and may enable continuation of the biopsy procedure with non-enhanced imaging techniques, thereby reducing or avoiding early termination of biopsy procedures due to contrast agent washout.

An example provides a method including determining a position of a biopsy target in a selected image of a patient based on an image registration process with a reference image of the patient and displaying a graphical representation of the position of the biopsy target on the selected image. In a first example of the method, the method further includes receiving a user input indicating the position of the biopsy target in a contrast-enhanced, dual energy image. In a second example of the method, which optionally includes the first example, the selected image is a non-contrast enhanced image, and further comprising receiving a user input requesting a switch from contrast-enhanced imaging to non-contrast enhanced imaging, and acquiring the selected image in response to the request. In a third example of the method, which optionally includes one or both of the first and second examples, determining the position of the biopsy target in the selected image based on the image registration process with the reference image comprises: tagging the position of the biopsy target in the reference image with a marker, wherein the reference image is a low energy image used to generate the dual energy image; and determining the position of the biopsy target in the selected image based on the position of the marker in the reference image, via the image registration process. In a fourth example of the method, which optionally includes one or more or each of the first through third examples, the image registration process comprises: selecting a plurality of control points in the reference image, calculating a local shift vector for each control point relative to a corresponding control point in the selected image, interpolating each pixel of the selected image based on each local shift vector to generate a motion vector field; and determining the position of the marker in the selected image based on the motion vector field. In a fifth example of the method, which optionally includes one or more or each of the first through fourth examples, the method further includes segmenting the dual energy image to identify a contour of the biopsy target, and wherein the marker is the contour. In a sixth example of the method, which optionally includes one or more or each of the first through fifth examples, the method further includes acquiring one or more additional images between acquisition of the reference image and acquisition of the selected image.

An example of a method includes receiving an indication of a location of a biopsy target in a contrast-enhanced, dual energy image; tagging the location with a marker in a reference dataset used to generate the dual energy image; annotating a subsequent image with the marker, a location of the marker in the subsequent image determined via an image registration process with the reference dataset; and outputting the annotated subsequent image for display on a display device. In a first example of the method, the reference dataset is a first low energy image and the subsequent image is a second low energy image. In a second example of the method, which optionally includes the first example, the method further includes determining the location of the marker in the second low energy image via the image registration process with the first low energy image by: selecting a plurality of control points in the first low energy image, calculating a local shift vector for each control point relative to a corresponding control point in the second low energy image, interpolating each pixel of the second low energy image based on each local shift vector to generate a motion vector field, and determining the location of the marker in the second low energy image based on the motion vector field. In a third example of the method, which optionally includes one or both of the first and second examples, the second low energy image is acquired after acquisition of the first low energy image, and further comprising acquiring one or more additional low energy images between acquisition of the first low energy image and acquisition of the second low energy image. In a fourth example of the method, which optionally includes one or more or each of the first through third examples, tagging the location with the marker comprises segmenting the reference dataset to determine a border of the biopsy target, and wherein annotating the subsequent image with the marker comprises annotating the subsequent image with the border. In a fifth example of the method, which optionally includes one or more or each of the first through fourth examples, receiving the indication of the location of the biopsy target comprises receiving the indication of the location of the biopsy target via a user input entered while the dual energy image is displayed on the display device. In a sixth example of the method, which optionally includes one or more or each of the first through fifth examples, the reference dataset is a first 3D volume and the dual energy image is a first reconstructed slice of the first 3D volume, and wherein the subsequent image is a second reconstructed slice of a subsequent, second 3D volume.

An example of an imaging system includes an x-ray source in communication with a detector; a display device; and a computing device connected in communication with the display device and the detector, the computing device including a processor and non-transitory memory storing instructions executable by the processor to: acquire, with the x-ray source and detector, a first low energy image of a patient and a first high energy image of the patient; recombine the first low energy image and the second high energy image to generate a dual energy image; output the dual energy image for display on the display device; receive a user input indicating a location of a biopsy target on the dual energy image; acquire, with the x-ray source and detector, a second low energy image of the patient; determine a position of the biopsy target in the second low image based on an image registration process with the first low energy image; and display, on the display device, the second low energy image and a graphical representation of the position of the biopsy target on the second low energy image. In a first example of the system, the instructions are further executable by the processor to, upon receiving the user input, segment the dual energy image to determine a border of the biopsy target; and wherein the graphical representation includes the determined border of the biopsy target. In a second example of the system, which optionally includes the first example, the instructions are executable by the processor to perform the image registration process with the first low energy image and the second low energy image by:

selecting a plurality of control points in the first low energy image, calculating a local shift vector for each control point relative to a corresponding control point in the second low energy image, interpolating each pixel of the second low energy image based on each local shift vector to generate a motion vector field, and determining the location of the biopsy target in the second low energy image based on the motion vector field. In a third example of the system, which optionally includes one or both of the first and second examples, interpolating each pixel of the second low energy image based on each local shift vector to generate the motion vector field comprises performing a first interpolation based on each local shift vector to generate a respective motion vector for each pixel. In a fourth example of the system, which optionally includes one or more or each of the first through third examples, determining the location of the biopsy target in the second low energy image based on the motion vector field comprises performing a second interpolation based on each motion vector to determine the location of the biopsy target in the second low energy image. In a fifth example of the system, which optionally includes one or more or each of the first through fourth examples, the instructions are executable by the processor to determine a position of the biopsy target in any additional low energy images of the patient based on an image registration process with the first low energy image.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:
   determining a position of a biopsy target in a selected image of a patient based on an image registration process with a reference image of the patient;
   displaying a graphical representation of the position of the biopsy target on the selected image, wherein the selected image is a non-contrast enhanced image;
   receiving a user input indicating the position of the biopsy target in a contrast-enhanced, dual energy image; and
   receiving a user input requesting a switch from contrast-enhanced imaging to non-contrast enhanced imaging, and acquiring the selected image in response to the request.

2. The method of claim 1, wherein determining the position of the biopsy target in the selected image based on the image registration process with the reference image comprises:
   tagging the position of the biopsy target in the reference image with a marker, wherein the reference image is a low energy image used to generate the dual energy image; and
   determining the position of the biopsy target in the selected image based on the position of the marker in the reference image, via the image registration process.

3. The method of claim 2, wherein the image registration process comprises:
   selecting a plurality of control points in the reference image,
   calculating a local shift vector for each control point relative to a corresponding control point in the selected image,
   interpolating each pixel of the selected image based on each local shift vector to generate a motion vector field, and
   determining the position of the marker in the selected image based on the motion vector field.

4. The method of claim 2, further comprising segmenting the dual energy image to identify a contour of the biopsy target, and wherein the marker is the contour.

5. The method of claim 1, further comprising acquiring one or more additional images between acquisition of the reference image and acquisition of the selected image.

6. A method, comprising:
   receiving an indication of a location of a biopsy target in a contrast-enhanced, dual energy image;
   tagging the location with a marker in a reference dataset used to generate the dual energy image;
   annotating a subsequent image with the marker, a location of the marker in the subsequent image determined via an image registration process with the reference dataset; and
   outputting the annotated subsequent image for display on a display device.

7. The method of claim 6, wherein the reference dataset is a first low energy image and wherein the subsequent image is a second low energy image.

8. The method of claim 7, further comprising determining the location of the marker in the second low energy image via the image registration process with the first low energy image by:
   selecting a plurality of control points in the first low energy image,
   calculating a local shift vector for each control point relative to a corresponding control point in the second low energy image,
   interpolating each pixel of the second low energy image based on each local shift vector to generate a motion vector field, and
   determining the location of the marker in the second low energy image based on the motion vector field.

9. The method of claim 7, wherein the second low energy image is acquired after acquisition of the first low energy image, and further comprising acquiring one or more additional low energy images between acquisition of the first low energy image and acquisition of the second low energy image.

10. The method of claim 6, wherein tagging the location with the marker comprises segmenting the reference dataset to determine a border of the biopsy target, and wherein annotating the subsequent image with the marker comprises annotating the subsequent image with the border.

11. The method of claim 6, wherein receiving the indication of the location of the biopsy target comprises receiving the indication of the location of the biopsy target via a user input entered while the dual energy image is displayed on the display device.

12. The method of claim 6, wherein the reference dataset is a first 3D volume and the dual energy image is a first reconstructed slice of the first 3D volume, and wherein the subsequent image is a second reconstructed slice of a subsequent, second 3D volume.

13. An imaging system, comprising:
an x-ray source in communication with a detector;
a display device; and
a computing device connected in communication with the display device and the detector, the computing device including a processor and non-transitory memory storing instructions executable by the processor to:
acquire, with the x-ray source and detector, a first low energy image of a patient and a first high energy image of the patient;
recombine the first low energy image and the second high energy image to generate a dual energy image;
output the dual energy image for display on the display device;
receive a user input indicating a location of a biopsy target on the dual energy image;
acquire, with the x-ray source and detector, a second low energy image of the patient;
determine a position of the biopsy target in the second low image based on an image registration process with the first low energy image; and
display, on the display device, the second low energy image and a graphical representation of the position of the biopsy target on the second low energy image.

14. The imaging system of claim 13, wherein the instructions are further executable by the processor to, upon receiving the user input, segment the dual energy image to determine a border of the biopsy target; and
wherein the graphical representation includes the determined border of the biopsy target.

15. The imaging system of claim 13, wherein the instructions are executable by the processor to perform the image registration process with the first low energy image and the second low energy image by:
selecting a plurality of control points in the first low energy image,
calculating a local shift vector for each control point relative to a corresponding control point in the second low energy image,
interpolating each pixel of the second low energy image based on each local shift vector to generate a motion vector field; and
determining the location of the biopsy target in the second low energy image based on the motion vector field.

16. The imaging system of claim 15, wherein interpolating each pixel of the second low energy image based on each local shift vector to generate the motion vector field comprises performing a first interpolation based on each local shift vector to generate a respective motion vector for each pixel.

17. The imaging system of claim 16, wherein determining the location of the biopsy target in the second low energy image based on the motion vector field comprises performing a second interpolation based on each motion vector to determine the location of the biopsy target in the second low energy image.

18. The imaging system of claim 13, wherein the instructions are executable by the processor to determine a position of the biopsy target in any additional low energy images of the patient based on an image registration process with the first low energy image.

* * * * *